US00PP29562P2

(12) United States Plant Patent
Barr

(10) Patent No.: US PP29,562 P2
(45) Date of Patent: Jul. 31, 2018

(54) ***ASPIDISTRA* PLANT NAMED 'BARR01'**

(50) Latin Name: *Aspidistra elatior*
Varietal Denomination: Barr01

(71) Applicant: William C. Barr, Rosenberg, TX (US)

(72) Inventor: William C. Barr, Rosenberg, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 15/731,818

(22) Filed: Aug. 7, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — C. A. Whealy

(57) ABSTRACT

A new and distinct cultivar of *Aspidistra* plant named 'Barr01', characterized by its compact and upright plant habit; relatively vigorous growth habit; relatively rapid production of divisions; glossy medium green-colored leaves; and durability with good landscape performance.

2 Drawing Sheets

Botanical classification: *Aspidistra elatior.*
Cultivar designation: 'Barr01'.

BACKGROUND OF THE INVENTION

The present invention relates to a new and distinct cultivar of *Aspidistra* plant, botanically known as *Aspidistra elatior*, commonly referred to as Cast Iron Plant and hereinafter referred to by the cultivar name 'Barr01'.

The new *Aspidistra* plant is a naturally-occurring whole plant mutation of an unnamed selection of *Aspidistra elatior*, not patented. The new *Aspidistra* plant was discovered and selected by the Inventor as a single plant from within a population of plants of the unnamed selection of *Aspidistra elatior* in a controlled nursery environment in Fulshear, Tex. in 2005.

Asexual reproduction of the new *Aspidistra* plant by divisions in a controlled environment in Fulshear, Tex. since 2007 has shown that the unique features of this new *Aspidistra* plant are stable and reproduced true to type in successive generations.

SUMMARY OF THE INVENTION

Plants of the new *Aspidistra* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barr01'. These characteristics in combination distinguish 'Barr01' as a new and distinct *Aspidistra* plant:

1. Compact and upright plant habit.
2. Relatively vigorous growth habit and relatively rapid production of divisions.
3. Glossy medium green-colored leaves.
4. Durable with good landscape performance.

Plants of the new *Aspidistra* differ primarily from plants of the mutation parent selection in the following characteristics:

1. Plants of the new *Aspidistra* are more compact than plants of plants of the mutation parent selection.
2. Leaves of plants of the new *Aspidistra* are upright whereas leaves of plants of the mutation parent selection are outwardly arching.
3. Leaves of plants of the new *Aspidistra* are smaller and have shorter petioles than leaves of plants of the mutation parent selection.
4. Plants of the new *Aspidistra* produce divisions twice as fast as plants of the mutation parent selection.

Plants of the new *Aspidistra* can be compared to plants of *Aspidistra elatior* 'Milky Way', not patented. In side-by-side comparisons, plants of the new *Aspidistra* differ primarily from plants of 'Milky Way' in the following characteristics:

1. Plants of the new *Aspidistra* are more compact than plants of plants of 'Milky Way'.
2. Leaves of plants of the new *Aspidistra* are solid green in color whereas leaves of plants of 'Milky Way' are green with white-colored spots.

BRIEF DESCRIPTION OF THE PHOTOGRAPHS

The accompanying colored photographs illustrate the overall appearance of the new *Aspidistra* plant showing the colors as true as it is reasonably possible to obtain in colored reproductions of this type. Colors in the photographs may differ slightly from the color values cited in the detailed botanical description which accurately describe the colors of the new *Aspidistra* plant.

The photograph on the first sheet is a side perspective view of a typical plant of 'Barr01' grown in a container.

The photograph on the second sheet is a side perspective view of typical plants of 'Barr01' (left) and the mutation parent, the unnamed selection of *Aspidistra elatior*, (right) grown in containers.

DETAILED BOTANICAL DESCRIPTION

Plants used for the aforementioned photographs and following observations, measurements and values were grown during the summer in three-gallon containers in an outdoor nursery in El Campo and Fort Worth, Tex. and under cultural practices typical of commercial *Aspidistra* production. Plants were two years old when the photographs and the description were taken. In the following description, color references are made to The Royal Horticultural Society Colour Chart, 2007 Edition, except where general terms of ordinary dictionary significance are used.

Botanical classification: *Aspidistra elatior* 'Barr01'.

Parentage: Naturally-occurring whole plant mutation of an unnamed selection of *Aspidistra elatior*, not patented.

Propagation information:

*Type*.—By divisions; production of divisions is relatively rapid.

*Time to initiate roots, summer*.—About 30 days at temperatures about 28° C.

*Time to initiate roots, winter*.—About 60 days at temperatures about 13° C.

*Time to produce a rooted young plant, summer*.—About 180 days at temperatures about 28° C.

*Time to produce a rooted young plant, winter*.—About 210 days at temperatures about 13° C.

*Root description*.—Thick, fleshy; typically creamy white in color, actual color of the roots is dependent on substrate composition, water quality, fertilizer type and formulation, substrate temperature and physiological age of roots.

*Rooting habit*.—Not freely branching; sparse.

Plant description:

*Plant form and growth habit*.—Compact and upright plant habit; relatively vigorous and produces divisions relatively rapidly; stemless and leaves basal.

*Plant height*.—About 34 cm.

*Plant width* (*spread*).—About 41 cm.

Leaf description:

*Arrangement*.—Basal, simple.

*Length*.—About 33 cm.

*Width*.—About 6.25 cm.

*Shape*.—Oblanceolate.

*Apex*.—Elongated acuminate.

*Base*.—Attenuate.

*Margin*.—Entire.

*Aspect*.—Mostly upright.

*Texture and luster, upper surface*.—Smooth, glabrous; glossy.

*Texture and luster, upper surface*.—Smooth, glabrous; slightly glossy.

*Venation pattern*.—Parallel.

*Color*.—Developing leaves, upper and lower surfaces: Close to 146A; venation, close to 146A. Fully expanded leaves, upper and lower surfaces: Darker than 146A; venation, darker than 146A.

*Petioles*.—Length: About 5.5 cm. Diameter: About 4 mm. Aspect: Upright. Strength: Strong, rigid. Texture and luster, upper and lower surfaces: Smooth, glabrous; glossy. Color, upper and lower surfaces: Distally, close to 146A; proximally, close to 154A.

Flower description: Flower initiation and development have not been observed on plants of the new *Aspidistra* to date.

Pathogen & pest resistance: Plants of the new *Aspidistra* have not been observed to be resistant to pathogens and pests common to *Aspidistra* plants.

Garden performance: Plants of the new *Aspidistra* have been observed to be durable and have good garden performance and to be tolerant to high temperatures about 44.4° C. and low temperatures about −17.7° C.

It is claimed:

1. A new and distinct *Aspidistra* plant named 'Barr01' as illustrated and described.

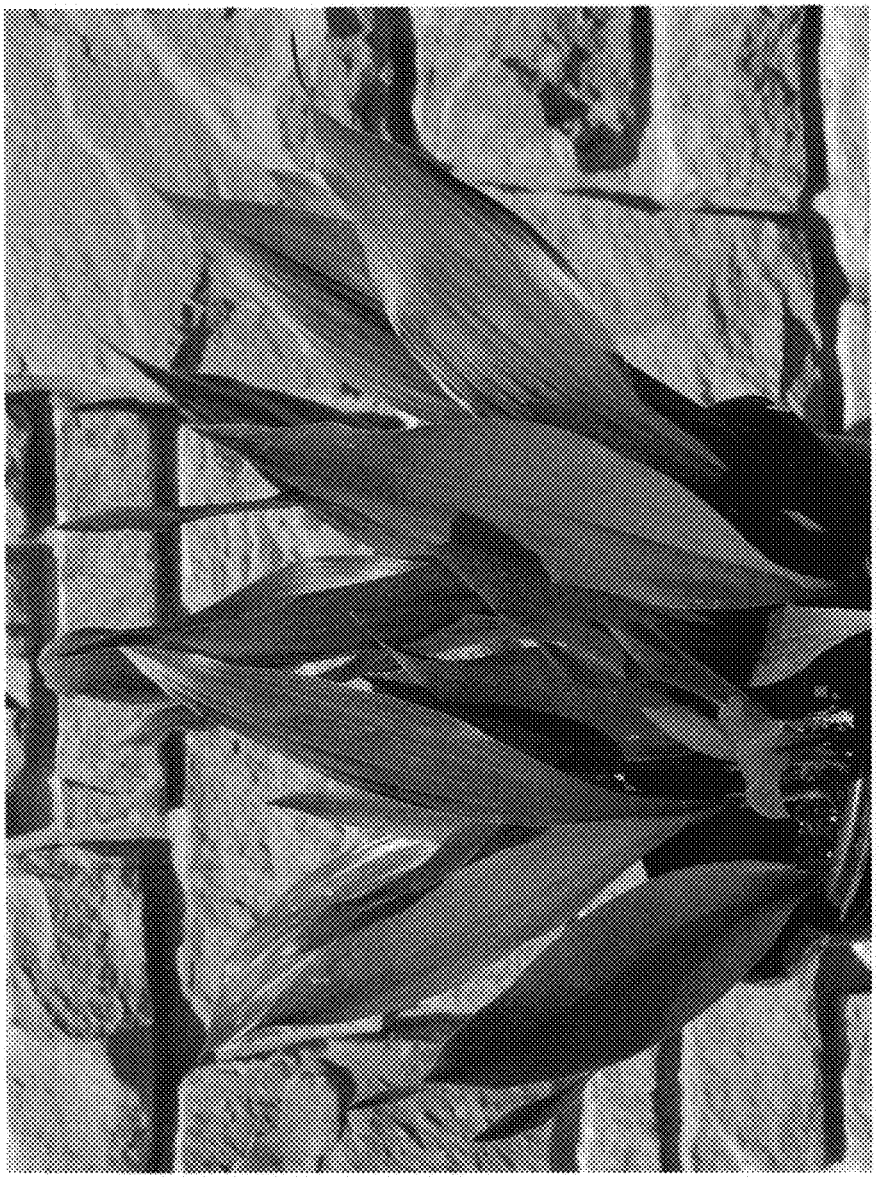

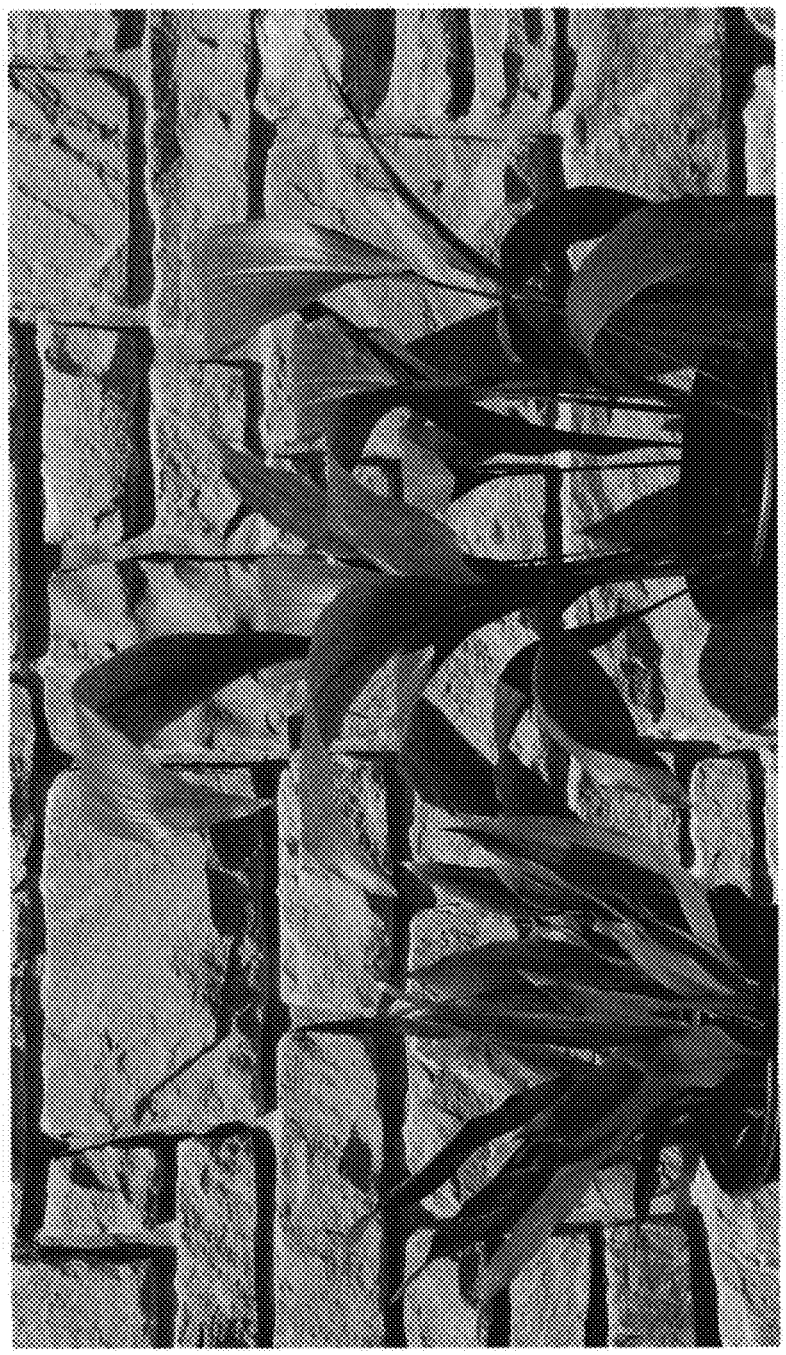

* * * * *